United States Patent [19]

Ohno et al.

[11] Patent Number: 4,795,587
[45] Date of Patent: Jan. 3, 1989

[54] 2-(4'-ALKOXYPHENYL)-5-ALKYLPYRIDINES

[75] Inventors: Kouji Ohno; Hiromichi Inoue; Takashi Inukai; Shinichi Saito; Kazutoshi Miyazawa, all of Kanagawa, Japan

[73] Assignee: Chisso Corporation, Ohsaka, Japan

[21] Appl. No.: 28,689

[22] Filed: Mar. 20, 1987

[30] Foreign Application Priority Data

Mar. 26, 1986 [JP] Japan ................... 61-67961

[51] Int. Cl.⁴ ................ G02F 1/13; C09K 19/34;
C07D 213/30; C07D 309/06
[52] U.S. Cl. ................ 252/299.61; 252/299.01;
252/299.5; 350/350 S; 546/339
[58] Field of Search ............ 252/299.61, 299.01,
252/299.5; 350/350 S, 350 R; 546/339

[56] References Cited

U.S. PATENT DOCUMENTS

| 4,622,165 | 11/1986 | Kano et al. | 252/299.01 |
| 4,684,220 | 8/1987 | Shionozaki et al. | 350/350 R |
| 4,684,477 | 8/1987 | Sugimori | 252/299.61 |

FOREIGN PATENT DOCUMENTS

| 194153 | 9/1986 | European Pat. Off. | 252/299.61 |
| 206228 | 12/1986 | European Pat. Off. | 252/299.61 |
| 3315295 | 10/1984 | Fed. Rep. of Germany | 252/299.61 |
| 3515374 | 11/1986 | Fed. Rep. of Germany | 252/299.61 |
| 3515373 | 11/1986 | Fed. Rep. of Germany | 252/299.61 |
| 61-91284 | 5/1986 | Japan | 252/299.61 |
| 62-155257 | 7/1987 | Japan | 252/299.61 |
| 2092169 | 8/1982 | United Kingdom | 252/299.61 |
| 2161808 | 1/1986 | United Kingdom | 252/299.61 |
| 8606401 | 11/1986 | World Int. Prop. O. | 252/299.61 |

OTHER PUBLICATIONS

Pavluchenko, A. I., et al., Advances in Liquid Crystal Research and Applications, Bata, L., Perlamom Press, Oxford, (1980) pp. 1007–1013.
Demus, O., et al., Flussige Kristalle in Tabellen II, Veb Deutscher Verlag fur Grumastoffindustrie, Leipeig, pp. 363–364 (1984).
Gray, G. W., et al., Liquid Crystals & Plastic Crystals, vol. 1, pp. 165–166, John Wiley & Sons, N.Y. (1974).

*Primary Examiner*—Teddy S. Gron
*Attorney, Agent, or Firm*—Wenderoth, Lind & Ponack

[57] ABSTRACT

A novel liquid crystal compound exhibiting SC phase which, when added to an optically active liquid crystal, makes the resulting chiral smectic liquid crystal material exhibit superior performances in liquid crystal display elements utilizing the ferroelectricity of the material, and a chiral smectic C composition using the compound, which compound is expressed by the formula

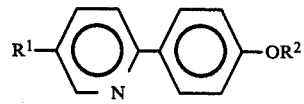

wherein $R^1$ represents an alkyl group of 7 to 12 carbon atoms and $R^2$ represents an alkyl group of 5 to 12 carbon atoms.

7 Claims, No Drawings

2-(4'-ALKOXYPHENYL)-5-ALKYLPYRIDINES

BACKGROUND OF THE INVENTION

1. Field of the Invention

This invention relates to a novel liquid crystal compound and a chiral smectic C liquid crystal composition containing the liquid crystal compound as a constituent thereof and being useful for liquid crystal display elements.

1. Description of the Related Art

At present, as to liquid crystal display elements, TN (Twisted Nematic) type display mode has been most broadly employed, but as far as the response speed is concerned, such TN type display elements are inferior to emissive type display elements (such as those of electroluminescence, plasma display, etc.). Although various improvements in this respect have been attempted, it appears that improvement to a large extent has not yet been realized. Thus, various liquid crystal display devices based on a different principle from that of TN type display elements have been attempted. As one of such devices, there is a display mode utilizing a ferroelectric liquid crystal (N. A. Clark et al: Applied Phys. lett., 36, 899 (1980)). This mode utilizes the chiral smectic C phase (hereinafter abbreviated to SC* phase) or the chiral smectic H phase (hereinafter abbreviated to SH* phase) of the ferroelectric) liquid crystal, and those having these phases in the vicinity of room temperature are preferred.

These chiral smectic liquid crystal materials may be obtained by blending a plurality of single compounds each exhibiting a chiral smectic phase by itself, but it is known that the materials may be also obtained by adding an optically active liquid crystal compound, preferably a chiral smectic liquid crystal compound to an achiral smectic liquid crystal exhibiting smectic C phase (SC phase), smectic H phase (SH phase), etc.

Various kinds of compounds exhibiting SC phase have already been known, but as to whether or not chiral smectic liquid crystal materials obtained by adding thereto an optically active liquid crystal exhibit superior performances in liquid crystal display utilizing ferroelectricity, no ultimate evaluation thereof has been yet obtained. This is due to the fact that liquid crystal display utilizing ferroelectricity has not yet been technically completed. Thus, in the present situation, it is necessary to test various novel SC materials.

SUMMARY OF THE INVENTION

The main object of the present invention is to provide a novel liquid crystal compound exhibiting SC phase which is suitable for the above-mentioned use.

The present invention resides in a liquid crystal compound expressed by the formula

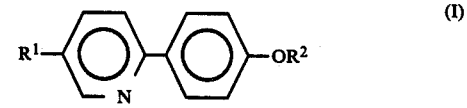

wherein $R^1$ represents an alkyl group of 7 to 12 carbon atoms and $R^2$ represents an alkyl group of 5 to 12 carbon atoms, and a chiral smectic liquid crystal composition containing at least one of said liquid crystal compounds and at least one kind of optically active liquid crystal compound.

DETAILED DESCRIPTION OF PREFERRED EMBODIMENTS

The phase transition points of the compounds of the formula (I) are shown in Table 1.

TABLE 1

| Sample No. | In formula (I) $R^1$ | $R^2$ | C | SH | SG | SF | SB | SC | SA | N | I |
|---|---|---|---|---|---|---|---|---|---|---|---|
| 1 | $C_7H_{15}$ | $C_5H_{11}$ | • 26.5 | — | • 35 | • 48 | — | • 67.5 | — | • 68.7 | • |
| 2 | $C_7H_{15}$ | $C_6H_{13}$ | • 34.0 | (• 31.2) | • 44.4 | • 53 | — | • 74.4 | — | • 75.2 | • |
| 3 | $C_7H_{15}$ | $C_7H_{15}$ | • 24.0 | • 31.5 | • 40.3 | • 53 | — | • 76.6 | — | — | • |
| 4 | $C_7H_{15}$ | $C_8H_{17}$ | • 45.0 | — | • 45.4 | • 56.5 | — | • 80.4 | — | — | • |
| 5 | $C_7H_{15}$ | $C_9H_{19}$ | • 42.5 | — | — | • 58.5 | — | • 80.7 | — | — | • |
| 6 | $C_7H_{15}$ | $C_{10}H_{21}$ | • 39.5 | — | — | • 62.0 | — | • 82.1 | — | — | • |
| 7 | $C_7H_{15}$ | $C_{11}H_{23}$ | • 48.8 | — | — | • 63.7 | — | • 81.4 | — | — | • |
| 8 | $C_7H_{15}$ | $C_{12}H_{25}$ | • 49.0 | — | — | • 67.0 | — | • 82.1 | — | — | • |
| 9 | $C_8H_{17}$ | $C_5H_{11}$ | • 37.4 | — | — | — | • 52.0 | • 70.1 | — | — | • |
| 10 | $C_8H_{17}$ | $C_6H_{13}$ | • 13.8 | • *(Sx) 15.0 | • 19.0 | • 54.0 | — | • 76.2 | — | — | • |
| 11 | $C_8H_{17}$ | $C_7H_{15}$ | • 27.3 | — | — | • 57.0 | — | • 77.5 | — | — | • |
| 12 | $C_8H_{17}$ | $C_8H_{17}$ | • 34.6 | — | — | • 60.2 | — | • 81.3 | — | — | • |
| 13 | $C_8H_{17}$ | $C_9H_{19}$ | • 37.5 | — | — | • 61.5 | — | • 81.4 | — | — | • |
| 14 | $C_8H_{17}$ | $C_{10}H_{21}$ | • 40.8 | — | — | • 65.5 | — | • 82.1 | — | — | • |
| 15 | $C_8H_{17}$ | $C_{11}H_{23}$ | • 47.3 | — | — | • 68.0 | — | • 82.2 | — | — | • |
| 16 | $C_8H_{17}$ | $C_{12}H_{25}$ | • 46.0 | — | — | • 70.2 | — | • 82.4 | — | — | • |
| 17 | $C_9H_{19}$ | $C_5H_{11}$ | • 42.5 | — | — | — | • 65.0 | • 72.4 | • 74.5 | — | • |
| 18 | $C_9H_{19}$ | $C_6H_{13}$ | • 36.0 | — | — | — | • 64.4 | • 80.5 | — | — | • |
| 19 | $C_9H_{19}$ | $C_7H_{15}$ | • 33.0 | — | — | — | • 64.0 | • 81.5 | — | — | • |
| 20 | $C_9H_{19}$ | $C_8H_{17}$ | • 31.6 | — | — | — | • 66.0 | • 85.1 | — | — | • |
| 21 | $C_9H_{19}$ | $C_9H_{19}$ | • 37.4 | — | — | — | • 69.6 | • 84.9 | — | — | • |
| 22 | $C_9H_{19}$ | $C_{10}H_{21}$ | • 38.6 | — | — | — | • 69.2 | • 86.3 | — | — | • |
| 23 | $C_9H_{19}$ | $C_{11}H_{23}$ | • 40.7 | — | — | — | • 75.4 | • 86.0 | — | — | • |
| 24 | $C_9H_{19}$ | $C_{12}H_{25}$ | • 43.5 | — | — | — | • 77.8 | • 85.2 | — | — | • |
| 25 | $C_{10}H_{21}$ | $C_5H_{11}$ | • 44.4 | — | — | — | • 66.7 | • 70.4 | • 74.7 | — | • |
| 26 | $C_{10}H_{21}$ | $C_6H_{13}$ | • 30.0 | — | — | — | • 67.6 | • 80.0 | — | — | • |
| 27 | $C_{10}H_{21}$ | $C_7H_{15}$ | • 41.0 | — | — | — | • 67.8 | • 80.8 | — | — | • |
| 28 | $C_{10}H_{21}$ | $C_8H_{17}$ | • 34.5 | — | — | — | • 71.2 | • 84.1 | — | — | • |
| 29 | $C_{10}H_{21}$ | $C_9H_{19}$ | • 40.7 | — | — | • 72.4 | — | • 84.0 | — | — | • |
| 30 | $C_{10}H_{21}$ | $C_{10}H_{21}$ | • 41.3 | — | — | • 75.8 | — | • 85.4 | — | — | • |
| 31 | $C_{10}H_{21}$ | $C_{11}H_{23}$ | • 47.6 | — | — | • 77.1 | — | • 85.2 | — | — | • |

TABLE 1-continued

| Sample No. | In formula (I) R¹ | R² | Phase transition points (°C.) C | SH | SG | SF | SB | SC | SA | N | I |
|---|---|---|---|---|---|---|---|---|---|---|---|
| 32 | $C_{10}H_{21}$ | $C_{12}H_{25}$ | • 48.0 | — | — | • 79.9 | — | • 86.1 | — | — | • |

*Sx means an unknown smectic phase

The compounds of the formula (I) of the present invention exhibit smectic C (SC) phase, and by blending the compound of the formula (I) mentioned later with other optically active liquid crystal compounds, particularly, chiral smectic liquid crystal compounds, it is possible to obtain a chiral smectic C liquid crystal composition exhibiting SC* phase within a broader temperature range. In this case, it is generally preferred to use a plurality of the compounds of the formula (I), and similar compounds exhibiting smectic C phase may be contained in addition to the compound of the formula (I).

Further, as the optically active liquid crystal compounds to be blended with those of the present invention, those exhibiting chiral smectic C phase are preferred, but even in the case of compounds exhibiting no chiral smectic C phase, there may be compounds affording a liquid crystal composition exhibiting chiral smectic C phase by blending such compounds with those of the present invention.

Here, homologues having a similar structure to that of the compound of the formula (I) of the present invention, that is, compounds in which the respective carbon numbers of $R_1$ and $R_2$ are outside the ranges of those of the compounds of the formula (I) of the present invention have been reported in a few literature publications. Thus, the relationship between these compounds and those of the present invention will be described below. Pavulchenko et al (L. Bata Ed.; Advances in Liquid Crystal Research and Application; Pergamon Press, 1980, page 1007) prepared compounds of the formula (I) wherein $R^1=C_4H_9$ and $R^2=CH_3$ or $C_4H_9$ and those wherein $R^1=C_6H_{13}$ and $R_2=CH_3$, $C_4H_9$, $C_5H_{11}$, $C_6H_{13}$ or $C_7H_{15}$ (seven kinds of compounds in total). They reported that among these compounds, those other than the compound of $R^1=C_6H_{13}$ and $R^2=C_5H_{11}$ exhibited at most one kind of smectic modification (however, what smectic phase the compound exhibits has not been decided), and the compound of $R^1=C_6H_{13}$ and $R^2=C_5H_{11}$ exhibited the following three kinds of smectic modifications ($S_1$ to $S_3$):

$$C \xrightarrow{21°C.} S_3 \xrightarrow{30°C.} S_2 \xrightarrow{43°C.} S_1 \xrightarrow{58°C.} N \xrightarrow{60.5°C.} I,$$

and they presumed that $S_1$ might perhaps be SA and $S_2$ might perhaps be SC. However, according to the research of the present inventors, this substance exhibits the following phase transitions:

$$C\xrightarrow{21°C.}S_H\xrightarrow{31°C.}S_G\xrightarrow{44°C.}S_F\xrightarrow{49°C.}S_C\xrightarrow{58°C.}N\xrightarrow{60.5°C.}I.$$

Further, Japanese patent application laid-open No. Sho 61-24570/1986 (filed by Suwa Seiko Company and laid-open on Feb. 3, 1986) discloses six compounds (a compound of $R^1=C_2H_5$ and $R^2=C_6H_{13}$; that of $R^1=C_5H_{11}$ and $R^2=C_2H_5$; that of $R^1=C_5H_{11}$ and $R^2=C_4H_9$; that of $R^1=C_5H_{11}$ and $R^2=C_5H_{11}$; that of $R^1=C_5H_{11}$ and $R^2=C_6H_{13}$; and that of $R^1=C_6H_{13}$ and $R^2=C_4H_9$), and indicates that these compounds are nematic liquid crystals or nonliquid crystalline compounds.

However, from such prior art it is not presumed that the compound of the formula (I) of the present invention exhibits $S_C$ phase.

Compounds of the formula (I) may be suitably prepared through the following route:

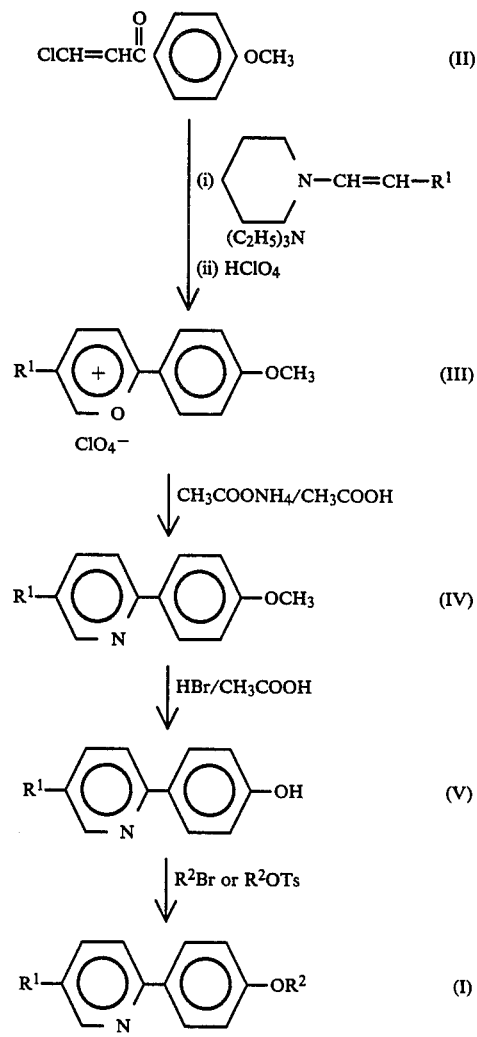

Namely, a known substance p-methoxyphenyl β-chlorovinyl ketone (II) is reacted with an enamine in the presence of triethylamine in a solvent and further reacted with perchloric acid to obtain a pyrylium perchlorate (III). The compound (III) is reacted with ammonium acetate in a solvent to obtain a compound (IV), which is then reacted with hydrobromic acid in a solvent (preferably, acetic acid) to obtain a compound (V), which is then heated together with an alkylbromide (or an alkyl tosylate) and potassium hydroxide to obtain the objective compounds of the formula (I).

The liquid crystal compound and liquid crystal composition of the present invention will be described in more detail by way of Examples.

EXAMPLE 1

Preparation of 2-[p-(octyloxy)phenyl]-5-heptylpyridine (a compound of the formula (I) wherein $R^1=C_7H_{15}$ and $R^2=C_8H_{17}$; sample No. 4)

(i) Preparation of 5-heptyl-2-(p-methoxyphenylpyrylium)perchlorate

N-heptenylpiperidine (41.8 g, 0.20 mol) and triethylamine (20 g, 0.20 mol) were dissolved in ethyl ether (100 ml) with stirring, followed by dropwise adding to the solution, a solution of p-methoxyphenyl β-chlorovinyl ketone (II) (39 g, 0.20 mol) and ethyl ether (200 ml) while keeping the temperature of the system at 35° C. or lower, agitating the mixture at room temperature for 8 hours, adding water (100 ml) and toluene (50 ml), washing the resulting organic layer with water, distilling off the solvent under reduced pressure, adding to the residue, 70% perchloric acid (100 ml), then adding water (100 ml), keeping the mixture under reflux for 10 minutes, cooling the resulting material to obtain crystals, washing the crystals with ethyl ether and drying them to obtain 5-heptyl-2-(p-methoxyphenylpyrylium)perchlorate (48.0 g).

(ii) Preparation of 5-heptyl-2-(p-methoxyphenyl)pyridine

5-Heptyl-2-(p-methoxyphenylpyrylium)perchlorate (48.0 g, 0.125 mol), ammonium acetate (96 g, 1.25 mol) and acetic acid (500 ml) were agitated under reflux for 4 hours, followed by pouring the resulting reaction fluid in water, dissolving the resulting crystals in toluene, washing them with water, distilling off the solvent under reduced pressure and recrystallizing the residue from methanol to obtain 5-heptyl-2-(p-methoxyphenyl)-pyridine (a compound of the formula (IV) wherein $R^1=C_7H_{15}$) (20 g), having a m.p. of 54.4°–56.5° C.

In addition, compounds of the formula (IV) wherein $R^1$ represents $C_8H_{17}$, $C_9H_{19}$ or $C_{10}H_{21}$ had the following melting points:

5-octyl-2-(p-methoxyphenyl)pyridine m.p. 60.7°–62.2° C.

5-nonyl-2-(p-methoxyphenyl)pyridine m.p. 55.0°–57.4° C.

5-decyl-2-(p-methoxyphenyl)pyridine m.p. 61.1°–62.9° C.

(iii) Preparation of 5-heptyl-2-(p-hydroxyphenyl)-pyridine

To 5-heptyl-2-(p-methoxyphenyl)pyridine (20 g, 0.071 mol) obtained in the above step (ii) (20 g, 0.071 mol) were added hydrobromic acid (47%) (130 ml) and acetic acid (300 ml), followed by keeping the mixture under reflux for 30 hours, cooling the resulting material, pouring it in water, filtering off the resulting crystals, dissolving the crystals in 2N-NaOH aqueous solution, further adding acetic acid to make the solution acidic, filtering off the deposited crystals and recrystallizing them from a mixture of methanol and water to obtain 5-heptyl-2-(p-hydroxyphenyl)pyridine (a compound of the formula (V) wherein $R^1=C_7H_{15}$) (13 g) having a m.p. of 105.2°–105.9° C.

In addition, compounds of the formula (V) wherein $R^1=C_8H_{17}$, $C_9H_{19}$ or $C_{10}H_{21}$ had the following melting points:

5-octyl-2-(p-hydroxyphenyl)pyridine m.p. 93.2°–95.0° C.

5-nonyl-2-(p-hydroxyphenyl)pyridine m.p. 85.0°–87.5° C.

5-decyl-2-(p-hydroxyphenyl)pyridine m.p. 90.4°–91.8° C.

(iv) Preparation of 2-[p-(octyloxy)phenyl]-5-heptylpyridine

5-Heptyl-2-(p-hydroxyphenyl)pyridine (10 g, 0.037 mol) obtained in the step (iii) together with ethanol (100 ml), potassium hydroxide (3.0 g, 0.045 mol) and octylbromide (9g, 0.048 mol) were heated under reflux with stirring for 4 hours, followed by cooling the resulting material, adding water and toluene, washing the resulting organic layer with 2N-NaOH aqueous solution, then washing it with water, distilling off the solvent under reduced pressure and recrystallizing the residue from ethanol to obtain the objective final product 2-[p-(octyloxy)phenyl]-5-heptylpyridine (6.5 g).

This product had a C-SG point of 45.0° C., a SG-SF point of 45.4° C., a SF-SC point of 56.5° C. and a SC-I point of 80.4° C.

The same procedure as above was carried out except that N-heptenylpiperidine used in the step (i) was replaced by other N-alkenylpiperidines and octylbromide used in the step (iv) was replaced by other alkylbromides or alkyl tosylates, to obtain all other compounds of the formula (I).

EXAMPLE 2

(Composition Example 1)

Four kinds of compounds of the present invention (sample Nos. 4, 7, 12 and 32) and a compound of the formula (I) except wherein $R^1=C_7H_{15}$ and $R^2=C_4H_9$, which compound has a similar chemical structure, but does not fall in the scope of the present invention and has the following phase transition points:

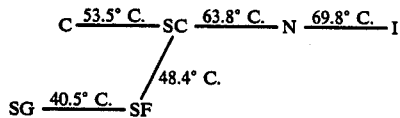

were blended in equal quantities to prepare a liquid crystal composition A.

This liquid crystal composition A had a m.p. of 12° C.; formed SB phase on the higher temperature side relative to the phase; formed SC phase at 52° C.; formed SA phase at 75° C.; and formed an isotropic liquid at 78° C.

To 60% by weight of this liquid crystal composition A were added and blended the following two kinds of chiral smectic liquid crystal compounds, each in an amount of 20% by weight, to prepare a chiral smectic liquid crystal composition B:

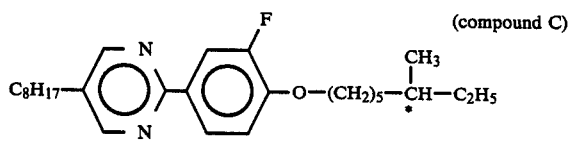

(compound C)

-continued (compound D)

$$C_6H_{13}\text{-}\bigcirc\text{-}O\overset{O}{\underset{\|}{C}}\text{-}\bigcirc\text{-}\bigcirc\underset{F}{\text{-}}\text{-}O\overset{CH_3}{\underset{*}{C}H}\text{-}C_6H_{13}$$

The resulting chiral smectic liquid crystal composition B had a m.p. of −10° C.; exhibited SC* phase in the temperature range higher than this temperature; formed SA phase at 54° C.; and formed an isotropic liquid at 68° C. Its supercooled state was observed down to −15° C.; it had SC* phase down to this temperature; and no other smectic phase was observed. In addition, the spontaneous polarization value was 10 nC/cm² at 25° C. and the tilt angle was 24° C.

A blend of the above compounds C and D in equal quantities had the following phase transition points:

$$C \xrightarrow{6.0° C.} SC^* \xrightarrow{48.4° C.} SA \xrightarrow{58.3° C.} I$$

The above-mentioned chiral smectic liquid crystal composition B was filled in a cell 2 μm thick provided with transparent electrodes having PVA (polyvinyl alcohol) as an aligning agent applied thereonto and subjected to parallel aligning treatment by rubbing the surface, and the resulting liquid crystal element was provided between two sheets of crossed polarizers and an electric field was impressed so that change in the intensity of transmitted light was observed by impression of 15 V.

Response time was sought from the change in the intensity of transmitted light at that time to give about 100 μsec. at 25° C.

As described above, it is seen that by blending the compound of the formula (I) of the present invention with an optically active liquid crystal compound, it is possible to obtain a ferroelectric chiral smectic C liquid crystal composition having a broad range of SC* phase and superior response properties.

EXAMPLE 3

(Composition Example 2)

Seven kinds of the compound of the present invention (sample Nos. 2, 4, 11, 13, 18, 22 and 24) were blended together in equal quantities to prepare a liquid crystal composition.

This liquid crystal composition was a smectic C composition and its phase transition points were as follows:

$$C \xrightarrow{11° C.} SB \xrightarrow{57.5° C.} SC \xrightarrow{80.1° C.} I$$

When this smectic C composition is blended with an optically active liquid crystal compound, it is possible to obtain superior chiral liquid crystal compositions as in the case of Example 2.

EXAMPLE 4

(Composition Example 3)

Four kinds of the compounds of the present invention (sample Nos. 1, 2, 9 and 17) and the following two compounds which have a similar structure, but do not fall in the scope of the present invention:

$$C_7H_{15}\text{-}\bigcirc_N\text{-}\bigcirc\text{-}OC_4H_9$$

$$(C \xrightarrow{53.5° C.} SC \xrightarrow{63.8° C.} N \xrightarrow{69.8° C.} I)$$
$$SG \xrightarrow{40.5° C.} SF \xrightarrow{48.4° C.}$$

and $$C_8H_{17}\text{-}\bigcirc_N\text{-}\bigcirc\text{-}OC_4H_9$$

$$(C \xrightarrow{32.7° C.} SB \xrightarrow{57.3° C.} SC \xrightarrow{66.8° C.} SA \xrightarrow{69.4° C.} I)$$

were blended together in equal quantities to prepare a liquid crystal composition.

This liquid crystal composition was a smectic C composition and its phase transition points were as follows:

$$C \xrightarrow{17° C.} SB \xrightarrow{51.0° C.} SC \xrightarrow{71.2° C.} I$$

When this smectic C composition is blended with an optically active liquid crystal compound, it is possible to obtain superior chiral liquid crystal compositions as in the case of Example 2.

What we claim is:

1. A liquid crystal compound expressed by the formula $$R^1\text{-}\bigcirc_N\text{-}\bigcirc\text{-}OR^2 \qquad (I)$$

wherein $R^1$ represents an alkyl group of 7 to 12 carbon atoms and $R^2$ represents an alkyl group of 5 to 12 carbon atoms, excluding the compound wherein $R^1$ is octyl and $R^2$ is heptyl.

2. A smectic C liquid crystal composition consisting of a plurality of liquid crystal compounds expressed by the formula (I) as set forth in claim 1.

3. A smectic C liquid crystal composition comprising at least one liquid crystal compound expressed by the formula (I) as set forth in claim 1.

4. A chiral smectic C liquid crystal composition comprising at least one liquid crystal compound expressed by the formula (I) as set forth in claim 1 and at least one optically active liquid crystal compound.

5. A chiral smectic C liquid crystal composition comprising a smectic C liquid crystal composition as set forth in claim 2 and at least one optically active liquid crystal compound.

6. A chiral smectic C liquid crystal composition comprising a smectic C liquid crystal composition as set forth in claim 3 and at least one optically active liquid crystal compound.

7. A light switching element which operates on the basis of ferroelectricity, said element containing a chiral smectic C liquid crystal composition comprising at least one liquid crystal compound expressed by the formula (I) as set forth in claim 1 and at least one optically active liquid crystal compound.

* * * * *